United States Patent [19]
Serafini et al.

[11] Patent Number: 5,338,827
[45] Date of Patent: Aug. 16, 1994

[54] POLYIMIDE RESINS USEFUL AT HIGH TEMPERATURES

[75] Inventors: Tito T. Serafini, Redlands; Paul G. Cheng, Rancho Palos Verdes; Kenneth K. Ueda, Lomita; Ward F. Wright, Redondo Beach, all of Calif.

[73] Assignee: TRW Inc., Redondo Beach, Calif.

[21] Appl. No.: 816,304

[22] Filed: Dec. 27, 1991

Related U.S. Application Data

[63] Continuation-in-part of Ser. No. 472,036, Jan. 30, 1990, Pat. No. 5,091,505, and a continuation-in-part of Ser. No. 472,198, Jan. 30, 1990, Pat. No. 5,132,395.

[51] Int. Cl.$^5$ .................. C08G 69/26; C08G 63/08; C08G 75/00; C08L 67/00
[52] U.S. Cl. .................. 528/353; 524/600; 524/879; 528/176; 528/288; 528/322; 528/342; 528/350; 528/352
[58] Field of Search .............. 528/353, 350, 352, 342, 528/288, 322, 176; 524/600, 879

[56] References Cited

U.S. PATENT DOCUMENTS

| | | | |
|---|---|---|---|
| 3,179,631 | 4/1965 | Endrey | 528/353 |
| 3,179,633 | 4/1965 | Endrey | 528/353 |
| 3,249,588 | 5/1966 | Gall | 528/353 |
| 3,407,176 | 10/1968 | Loncrini | 528/185 |
| 3,459,706 | 8/1969 | Schweitzer | 528/128 |
| 3,505,295 | 4/1970 | Grundsteidl et al. | 528/322 |
| 3,745,149 | 7/1973 | Serafini et al. | 528/288 |
| 3,998,786 | 12/1976 | D'Alelio | 528/353 |
| 4,058,505 | 11/1977 | D'Alelio | 528/353 |
| 4,061,856 | 12/1977 | Hsu | 528/353 |
| 4,094,862 | 6/1978 | Bell | 528/353 |
| 4,111,906 | 9/1978 | Jones et al. | 528/229 |
| 4,159,262 | 6/1979 | Hsu | 528/342 |
| 4,166,170 | 8/1979 | St. Clair | 528/229 |
| 4,173,700 | 11/1979 | Green et al. | 528/352 |
| 4,189,560 | 2/1980 | Roth et al. | 526/259 |
| 4,203,922 | 5/1980 | Jones et al. | 564/315 |
| 4,238,538 | 12/1980 | Manwiller | 428/35.7 |
| 4,302,413 | 11/1981 | Howe et al. | 264/126 |
| 4,391,967 | 7/1983 | Nimry et al. | 528/189 |
| 4,417,045 | 11/1983 | Nimry et al. | 528/188 |
| 4,440,643 | 4/1984 | Makino et al. | 210/500.28 |
| 4,456,653 | 6/1984 | Ruegg et al. | 428/379 |
| 4,497,948 | 2/1985 | Lauver | 528/342 |
| 4,499,042 | 2/1985 | Ishizuka et al. | 264/205 |
| 4,755,555 | 7/1988 | Manwiller et al. | 524/607 |
| 4,778,872 | 10/1988 | Sasaki et al. | 528/176 |
| 4,801,682 | 1/1989 | Scola | 528/353 |
| 4,963,645 | 10/1990 | Inoue et al. | 528/342 |
| 4,973,662 | 11/1990 | Odagiri et al. | 528/353 |
| 5,091,505 | 2/1992 | Serafini et al. | 528/353 |
| 5,132,395 | 6/1992 | Serafini et al. | 528/353 |
| 5,145,916 | 9/1992 | Yamamoto et al. | 525/432 |
| 5,149,760 | 9/1992 | Serafini et al. | 528/353 |
| 5,149,772 | 9/1992 | Serafini et al. | 528/353 |
| 5,162,492 | 11/1992 | Kaku | 528/353 |

FOREIGN PATENT DOCUMENTS

| | | |
|---|---|---|
| 0395020A2 | 10/1990 | European Pat. Off. |
| 0420593A2 | 4/1991 | European Pat. Off. |
| 0439915A1 | 8/1991 | European Pat. Off. |
| 0439916 | 8/1991 | European Pat. Off. |
| 57-26131 | 2/1982 | Japan |
| 63-172736 | 7/1988 | Japan |
| 63-248828 | 10/1988 | Japan |
| 1139632 | 1/1989 | Japan |
| 1135765 | 5/1989 | Japan |
| 3-9926 | 8/1992 | Japan |

OTHER PUBLICATIONS

Vannucci, R., *PMR Polyimide Compositions for Improved Performance at 371° C.*, SAMPE Quarterly, vol. 19, No. 1, Oct. 19, 1987, pp. 31-36.

(List continued on next page.)

*Primary Examiner*—John Kight, III
*Assistant Examiner*—T. Mosley

[57] ABSTRACT

Polyimide resins useful at high temperatures are prepared from:
(a) a dialkyl, trialkyl or tetraalkylester of biphenyltetracarboxylic acid;
(b) phenylenediamine, preferably the phenylenediamine comprises a mixture of meta-and para-phenylenediamine; and
(c) a divalent end cap compound that is capable of undergoing addition polymerization.

30 Claims, No Drawings

OTHER PUBLICATIONS

P. M. Hergenrother, *Condensation Polyimides*, in *Encyclopedia of Composites*, S. M. Lee, Ed. BCH Publisher, Inc., New York, vol. 4, 1991, pp. 180–196.

Meares, P., *Polymers Structure and Bulk Properties*, D. Van Nostrand Company, Ltd., London, p. 265.

Proceedings of the AFR-700 Symposium, dated Sep. 24, 1991.

PCT Search Report mailed on Nov. 2, 1992, for PCT/US92/03285.

T. T. Serafini, P. Delvigs and G. R. Lightsey, J. Appl. Polym. Sci., 16, 905 (1972).

P. Delvigs, T. T. Serafini, and C. F. Lightsey, *Addition Type Polyimides from Solutions of Monomeric Reactants*, NASA TN D-6877, Aug. '72, also submitted to *Materials for '72, SAMPE*, Azusa, Calif. 1972.

T. L. St. Clair and R. A. Jewell, *Solventless LARC-160 Polyimide Matrix Resin*, NASA TM-74944, National Aeronautics and Space Administration, Washington, D.C., 1978.

T. T. Serafini and R. D. Vannucci, in *Tailor Making High Performance Graphite Fiber Reinforced PMR Polyimides*, NASA TMX-71616, Society of Plastics Industry, Inc., New York, 1975.

T. T. Serafini, R. D. Vannucci and W. B. Alston, *Second Generation PMR Polyimides*, NASA TM-71894, Washington, D.C. 1976.

P. Delvigs, *Investigation of a 700° F. Laminating Resin*, Proceedings of Second Technical Conference on Polyimides, Ellenville, New York, Nov. 1985.

T. T. Serafini, *Processable High Temperature Resistant Polymer Matrix Materials*, Proceedings ICCM I, vol. 1, AIME, New York, p. 202, 1976.

F. I. Hurwitz, *Influence of Excess Diamine on Properties of PMR Polyimide Resins and Composites*, NASA TM-81580, 1980.

R. D. Vannucci, *PMR Polyimide Compositions for Improved Performance at 371° C.*, NASA, SAMPE Apr. 6–9, 1987.

Matrix Resin Development, vol. II, Technical Proposal, Feb. 29, 1988.

Technical Progress Reports Entitled *Matrix Resin Development* from TRW to Northrop Corp.

Structural Composite Materials (STRCM), AFWAL/AFML/DARPA Contract No. F33615-88-0-5409 Interim Report for period of Feb. 1989–Jul. 1989.

Submission to the General Electric Company for study entitled: *Processable 700° F. Matrix Resins*, Sep. 28, 1987.

T. T. Serafini, *High-Temperature Resins*, Chapter 6 in *Handbook of Composites*, G. Lubin, Ed., Van Nostrand Reinhold, 1982, pp. 89–113.

Serafini, T., *PMR Polyimide Composites for Aerospace Applications*, in *Polyimides*, edited by K. L. Mittal, Plenum Press, New York, pp. 957–975.

Morrison and Boyd, *Organic Chemistry*, 3d Ed., Allyn and Bacon, Boston, p. 730.

Browning, C., *New Applications for New Materials*, in Margolis, J., *Advanced Thermoset Composites*, Van Nostrand Reinhold, New York, pp. 1–20.

Billmeyer, Jr., F., *Textbook of Polymer Science*, 2d Ed., John Wiley and Sons, Inc., New York, p. 231.

Letter to P. G. Cheng, from Air Force, Jun. 25, 1990.

Dexter Corporation, News Release, *AFR-700 Resins*, Feb. 15, 1991, and customer list/amount sold as of Jun. 25, 1990, Cleveland, Ohio.

TRW, News Release, *TRW Develops Markets New High Temperature Polymer Family*, Nov. 7, 1991. TRW, Redondo Beach, Calif.

Brown, Alan, *The Air Force Finds an Ultrahigh-Temperature Resin*, Materials Notebook, Aerospace America, Oct. 1991.

U.S. Pat. No. application Ser. No. 07/472,198, filed Jan. 30, 1992, by Serafini et al.

POLYIMIDE RESINS USEFUL AT HIGH TEMPERATURES

CROSS-REFERENCE

This application is a continuation-in-part of copending U.S. patent application Ser. No. 07/472,036, U.S. Pat. No. 5,091,505, filed on Jan. 30, 1990, by the same inventors, and entitled "POLYIMIDE RESINS PREPARED BY ADDITION REACTIONS," which is incorporated herein by this reference, and copending U.S. patent application Ser. No. 07/472,198, U.S. Pat. No. 5,132,395, filed on Jan. 30, 1990, by the same inventors, and entitled "POLYIMIDE RESINS PREPARED BY ADDITION REACTIONS," which is also incorporated herein by this reference.

This invention relates to polyimide resins, a class of organic polymers known for their outstanding thermo-oxidative stability.

Polyimide resins are used to form the matrix of fiber-reinforced composite materials. These types of composite materials are increasingly used as the preferred structural materials in military and civil applications such as jet engine cowls and ducts, because of their light-weight and load-bearing characteristics and their oxidative stability at temperatures between 500° and 700° F.

Upper use temperature in conjunction with processing cost considerations determine the true value of a polyimide. Glass transition temperature ($T_g$) and thermo-oxidative stability are key determinants of upper use temperature. In order to use a polyimide composite for a load bearing application at a given temperature, the resin must have a $T_g$ substantially above that given temperature, otherwise the resin will soften and the composite will undergo creep. Thermo-oxidative stability is commonly measured as the percent weight loss during long term aging at high temperatures in an oxidative environment. Materials that rapidly lose weight have a short use life at that temperature.

Processing costs include cost of monomers, handling costs, and fabrication costs. Ideally, the polyimide resin should be prepared from low cost, minimally hazardous, starting chemicals. It should be readily converted into fiber reinforced prepreg tapes. Most importantly the prepreg tapes must be easily molded into void-free parts in standard composite fabrication equipment known as an autoclave. Materials that have insufficient flow under 200 psi, the maximum operating pressure for the vast majority of autoclaves, have little commercial utility.

Polyimides are generally prepared either through direct condensation reactions to afford linear, long chain, polyimides, or through addition reactions performed on end-capped imide oligomers to give cross-linked polyimides. In both cases, it is well known that high stability is conferred by the use of aromatic or heteroaromatic moieties, while the use of aliphatic moieties reduces thermal-oxidative stability.

Condensation type polyimides have the highest thermal-oxidative stability because aliphatic end caps (which are used in addition type polyimides) are not used. Condensation type polyimides are typically prepared by treating an aryl dianhydride with an aryl diamine in an aprotic solvents, such as N-methyl-pyrrolidinone, to produce a high molecular weight polyamide acid, which is subsequently dehydrated to give the final linear polyimide.

Condensation polyimides typically exhibit good oxidative stability but have found little practical use as composite matrix resins, because of substantial processing problems. For example, the polyamide acid is prone to solvolytic degradation and thus its shelf life can be only a few hours at ambient temperature. Therefore, the polyamide acid requires special handling and storage under refrigeration, which creates inconveniences that greatly increase the ultimate cost to the user. Also, impregnation of fibers with the highly viscous polyamic acid requires pressures of between 200 and 6000 psi. Costs associated with fabricating parts under these conditions are prohibitive for most applications. Furthermore, evolution of water and high boiling point solvents during curing result in unacceptably high void contents within the molded parts. These voids result in inferior mechanical properties and reduced thermo-oxidative stability.

Processing problems associated with condensation type polyimides have been overcome through the use of addition polymerization type polyimides. U.S. Pat. No. 3,745,149 discloses a method for forming addition type polyimides, whereby void-free polyimide composites can be readily fabricated. This invention involves the preparation of thermosetting polyimides via a solution of monomeric reactants which react in situ to form double end cap intermediates. This patent discloses a method for preparing polyimides from mixtures of (a) an dialkyl ester of an aromatic tetracarboxylic acid, (b) an aromatic diamine, and (c) an monoalkyl ester of a dicarboxylic acid (as an end cap) in a molar ratio of n:(n+1):2. The monomers are mixed in an alcoholic solvent, reacted at elevated temperatures to form, in situ, imide oligomers having end caps at both ends, and cured at high temperatures to yield macromolecular polyimides. Polyimide resins prepared by this method are conventionally referred to as PMR resins. The monomeric reactant solution can be readily used to make prepreg tapes that are autoclave processable.

Polyimide formulations prepared according to the method of U.S. Pat. No. 3,745,149, when reinforced with various fibers, have sufficient thermal stability and mechanical properties to serve as structural materials during continuous exposure at 550° F. These composites have successfully replaced metals as structural materials in applications such as jet engine cowls and ducts. A polyimide formulated according to U.S. Pat. No. 3,745,149 and commonly referred to as PMR-15 has gained wide acceptance in structural applications where thousands of hours of mechanical strength retention at 500°–600° F. is required. However, PMR-15 cannot be used at higher temperatures because neither its $T_g$ (about 630° F.) nor its thermo-oxidative stability is adequate. Furthermore, serious concern about the safety of PMR-15 has been raised because one of its key ingredients, methylene dianiline, is a carcinogen.

Attempts to prepare polyimides that can be used at temperatures above 550° F. according to the methodology described in U.S. Pat. No. 3,745,149 have been unsuccessful. See, for instance, R. Vannucci, *SAMPE Quarterly*, 19, (1), 31 (1987) and references cited therein. Typically, attempts have been made to synthesize higher molecular weight (about 3000) imide oligomers to minimize the contents of the aliphatic end-caps and thereby improve the thermal-oxidative stability. However, as the molecular weights of the imide oligomers increase, the resin flow decreases. Polyimides formulated according to U.S. Pat. No. 3,745,149 and having molecular weights high enough to withstand long term exposure at 700° F. in air have been found to require pressures of between 2000 and 5000 psi for proper consolidation. The processing of conventional high molecular weight imide oligomers thus can not be conducted with autoclaves, a hurdle that renders polyimides prepared according to U.S. Pat. No. 3,745,149 impractical for use at temperatures substantially above 550° F.

Our copending applications Ser. No. 07/472,036 U.S. Pat. No. 5,091,505 and Ser. No. 07/432,198, U.S. Pat. No. 5,132,395, describe the preparation of thermosetting polyimides via monomeric solutions which react in situ to form single end cap intermediates. The intermediates derived from application 07/472,198 have an amine terminal moiety and those derived from application 07/472,036 have an anhydride terminal moiety. These intermediate imides are both readily processable and can be used to prepare polyimide composites having higher $T_g$ and higher thermo-oxidative stability than PMR-15 polyimides. Two polyimides formulated according to these inventions, designated as AF-R-700A and B, can be continuously used at temperatures up to 700° F.

The polyimides processed via the methods described in our copending applications are subject to two limitations. First, many applications demand materials with use temperatures higher than 700° F. Furthermore, the monomers used to synthesize AF-R-700A and B are costly. In order to facilitate large scale adoption of polyimide composites, affordable systems with good processability and high temperature performance are needed.

Accordingly, there is a need for compositions of matter and methods for preparing addition type polyimide resins, where the resins can be easily prepared, composites containing the resins can be prepared using conventional autoclave equipment, the resins are affordable and non-toxic, and the resins have the capability of extended operation at elevated temperatures in excess of 700° F.

SUMMARY

The present invention provides polyimide resins and methods for their manufacture that satisfy this need. Polyimide resins prepared in accordance with the present invention have high temperature capability, excellent processability, physical properties superior to those of prior art addition type polyimide resins, and can be prepared from low cost monomers.

A composition of matter suitable for preparing these polyimide resins consists essentially of a mixture of the monomers:

(a) a dialkyl, trialkyl or tetraalkylester of biphenyltetracarboxylic acid;

(b) phenylenediamine; and (c) a divalent end cap compound characterized by (i) having at least one unsaturated moiety, (ii) being capable of reacting with the aromatic diamine or the ester to form an end cap radical that precludes further reaction of the aromatic diamine with the ester, and (iii) being capable of undergoing addition polymerization.

The molar ratio of (a), (b), and (c) is such that heating the mixture forms low molecular weight prepolymers having at least one end cap radical and suitable for chain extension and crosslinking to form high molecular weight, thermally stable polyimides. Typically the prepolymers have a molecular weight less than about 50,000, and generally less than about 10,000. These prepolymers can undergo facile crosslinking at elevated temperature under 200 psi to form macromolecular polyimides with use temperatures as high as 800° F.

The chemical structure, terminal moieties, and formulated molecular weights of the prepolymers depend on the molar ratio of the reactants. Either singly or double end cap intermediate polyimides can be obtained by adjusting the stoichiometry of reactants.

When the molar ratio of a:b:c is n:n+1:2 and the end cap compound reacts with the amine, the prepolymer has a double end cap structure with the following formula:

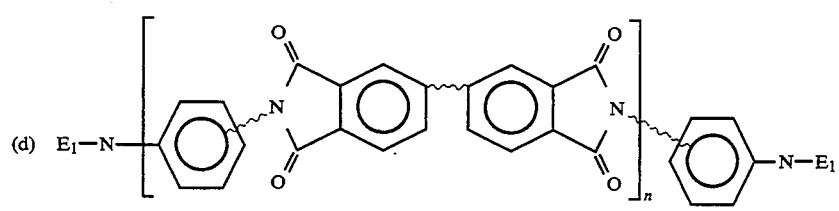

Compound 1

(d)

where $E_1$ is independently an end cap radical provided by the end cap compound.

When the molar ratio of a:b:c: is n:n:1, and the end cap compound reacts with the amine, the prepolymer has a single endcap, with an anhydride terminated structure having the formula:

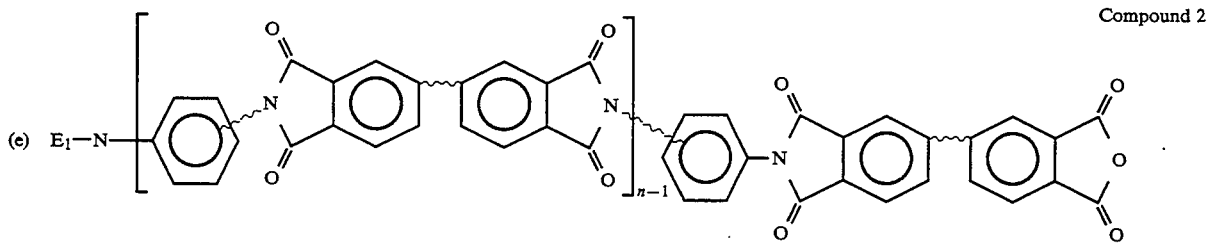

Compound 2

(e)

When the molar ratio of a:b:c: is n:n+1:1 and the end cap compound reacts with the amine, the prepolymer has a single endcap, with an amine terminated structure having the following formula:

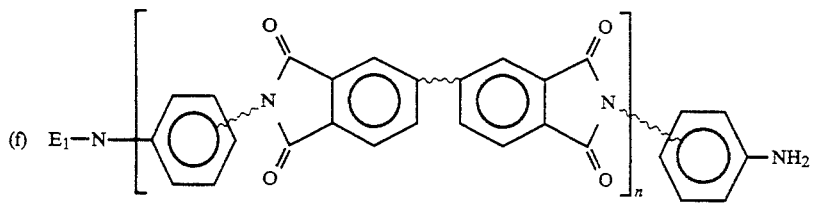

Compound 3

When the molar ratio a:b:c: is n+1:n:2, and the end cap compound reacts with the ester, the prepolymer has a double end cap structure having the following formula:

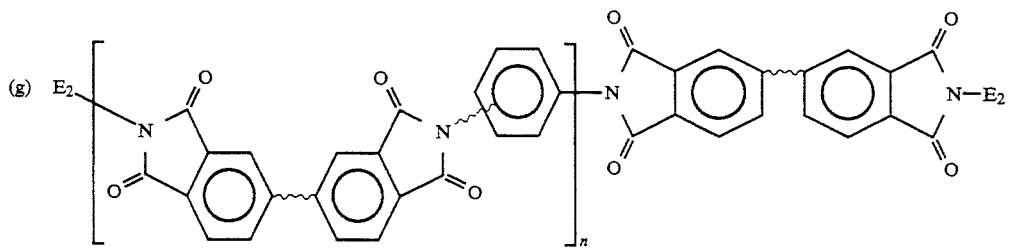

Compound 4 where $E_2$ is independently an end cap radial provided by the end cap compound.

When the molar ratio of a:b:c: is n+1:n:1 and the end cap compound reacts with the ester, the prepolymer has a single end cap, with an anhydride terminated structure having the following formula:

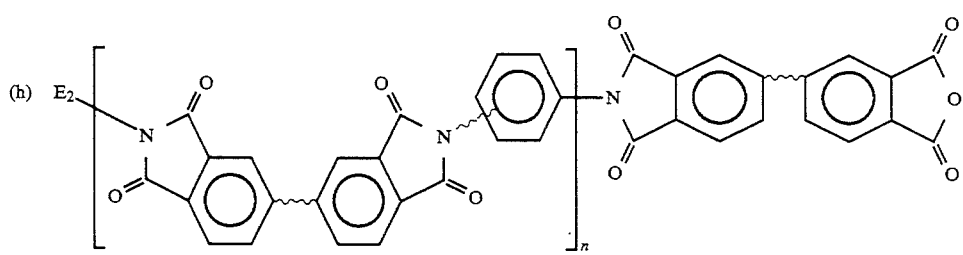

Compound 5

When the molar ratio of a:b:c: is n:n:1 and the end cap compound reacts with the ester, the polymer has a single endcap, with an amine terminated structure having the following formula:

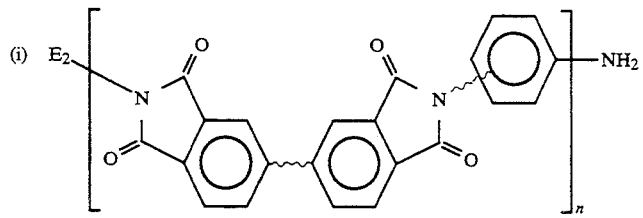

Compound 6

The bonds depicted by wavy lines represent variable structural configurations, i.e., such as the meta- or para-configurations, or different isomers of the biphenyl moiety.

To obtain high temperature properties and good processability, preferably the phenylenediamine comprises meta-phenylenediamine, and more preferably, consists essentially of meta-phenylenediamine alone, or a mixture of meta-phenylenediamine and para-phenylenediamine. In other words, at least a portion of the nitrogen of the phenylenediamine structure are in the meta position. For the doubly end-capped versions of the invention (compounds 1 and 4), the phenylenediamine always contains some meta-phenylenediamine to obtain good processability.

The composition of matter can also include an organic solvent, where the monomers comprise from about 30 to about 90 percent by weight of the solution.

A process for preparing a composite with a polyimide resin matrix, from the monomer composition, comprises mixing the monomer composition with a solvent, and then impregnating fibers with the resultant mixture. The impregnated fibers are then heated to a sufficiently high temperature to remove the solvent. The polyimide prepolymers are formed when the impregnated fibers are heated to at least about 375° F. When these prepolymers are heated to a temperature of at least about 690° F. crosslinking occurs, providing polyimide resins having a high molecular weight in excess of 50,000. A long post-curing cycle, with temperatures of at least about 600° F. for at least about 12 hours, enhances the physical properties of the polyimide resins.

The polyimide resins can be formed into complex shapes using autoclave and molding equipment. Polyimide resins of this invention have better physical properties than prior art addition type polyimide resins, including higher glass transition temperature ($T_g$) and high temperature stability. For example, $T_g$'s greater than 800° F. have been achieved In addition, the new polyimide resins can exhibit a weight loss of less than 5% when heated in air at 700° F. for 100 hours. Accordingly, composites comprising fibers reinforcing these polyimide resins can be used in high temperature applications for which addition type polyimide resins have heretofore been unsatisfactory or too expensive.

These and other features, aspects, and advantages of the present invention will become better understood with reference to the following description and appended claims.

DESCRIPTION

According to this invention, high temperature polyimides are synthesized from a mixture of the following monomer compounds:

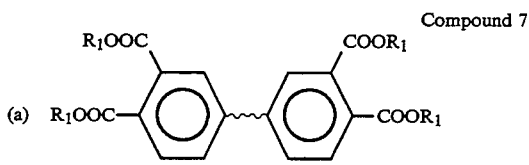

Compound 7 where $R_1$ is an alkyl, preferably lower alkyl of one to four carbon atoms, or hydrogen, at least two of $R_1$ being alkyl;

(b) $H_2N-R_2-NH_2$  Compound 8 wherein $R_2$ is a divalent phenyl moiety; and (c) a divalent endcap compound characterized by (i) having at least one unsaturated moiety, (ii) being capable of reacting with the aromatic diamine or the ester to form an endcap radical that precludes further reaction of the aromatic diamine with the ester, and (iii) being capable of undergoing addition polymerization. These compounds are combined to form prepolymers which are then used to form high molecular weight polyimide resins.

Esters

The esters of biphenyltetracarboxylic acid of Compound 7 can be prepared readily from the corresponding dianhydrides of the formula:

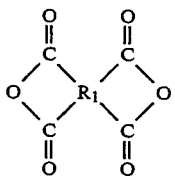

Compound 9 in which $R_1$ is a divalent phenyl moiety. For example, the ester can be conveniently prepared from the 3,3',4,4' biphenyltetracarboxylic dianhydride, or its isomers, such as 2,3,3',4' or 2,2',3,3' biphenyltetracarboxylic dianhydride.

Diamines

Representative diamines of the type of Compound 4 defined above include meta-phenylenediamine and para-phenylenediamine. It has been determined that excellent high temperature properties are obtained if the diamine consists primarily of only para-phenylenediamine. However, a mixture of monomers containing as the diamine only the para-phenylenediamine has a short shelf life. By "shelf life" there is meant the amount of time the mixture of monomer compounds (a), (b) and (c) can be stored at room temperature and used to impregnate fiber for preparing polyimide composites. It is important for many commercial applications that the shelf life be at least 24 hours. It has been discovered that in order to obtain this shelf life, it is important that phenylenediamine contain some meta-phenylenediamine, and preferably that the phenylenediamine consists essentially of only meta-phenylenediamine, or a mixture of meta- and para-phenylenediamine. Preferably the ratio of meta-phenylenediamine to para-phenylenediamine is at least about 1:1, and more preferably is from about 3:2 to about 4:1.

Compounds 2 and 5 are shown as being anhydrides. However, the exact structure of any of compounds 1-6 is unknown; thus the structures presented are those most likely from the monomers used to prepare the compounds. Compounds 2 and 5 could just as likely be esters rather than anhydrides. Thus, although compounds 2 and 5 are shown in this description and the claims as being anhydrides, the formulas are intended to represent the ester equivalents of the anhydrides.

Through the use of phenylenediamine, this invention avoids the danger of toxicity associated with the use of amines such as 4,4'-methylenedianiline, without sacrificing the physical properties of the final product.

End Cap

The end cap compounds control the average molecular weight of oligomers or prepolymers formed by condensation polymerization of the ester (a) and diamine (b) by reacting with either the ester or diamine. When the end cap compound reacts with the diamine to produce $E_1$, the end cap compound can be:

Compound 10 where at least one of $R_2$ is alkyl and $R_3$ is a divalent radical of the formulas:

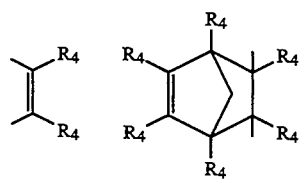

Compounds 11, 12 where each $R_4$ is independently selected from the group consisting of hydrogen and lower alkyls, normally one to four carbon atoms.

The mono- or dialkyl ester of the dicarboxylic acid (compound 10) can be prepared from the corresponding anhydride. Representative of such dianhydrides include maleic anhydride, citraconic anhydride, 5-norbornene--2,3-dicarboxylic anhydride, and alkyl or alkenyl substituted 5-norbornene-2,3-dicarboxylic anhydride.

Suitable end cap compounds for reacting with the ester to produce $E_2$ are amino compounds with the structure $R_6NH_2$, where $R_6$ is a moiety capable of addition polymerization. These include p-ethynylaniline (p-aminophenyllacetylene), p-aminostyrene, and (4-aminobenzo) cyclobutene.

Preparation of Polyimides

To prepare the polyimides of this invention, the ester, diamine, and end cap compound are dissolved in an organic solvent. Representative solvents include aliphatic alcohols, aliphatic ethers, aprotic solvents, N,N-dimethylformamide, and dimethylsulfoxide. Mixtures of two or more of such solvents can be employed. The solvents are inert to the monomers. The solutions of the esters and diamine have excellent shelf stability.

To prepare polyimides from this mixture of monomers, first the mixture is heated to a sufficiently high temperature to evaporate the solvent, generally in the order of about 120° F. to about 250° F. Then the mixture is heated to a sufficiently high temperature to form the prepolymers, generally a temperature of at least about 375° F. It is also preferred to react the mixture of monomers by heating in the presence of reinforcing fibers, to form the intermediate polyimides.

The structure, terminal moieties and formulated molecular weights of the prepolymers depend on the molar ratio of the reactants. Either single or double end cap intermediate polyimides can be obtained by adjusting the stoichiometry of reactants. These polyimide intermediates can undergo facile crosslinking at elevated temperature under 200 psi to form macromolecular polyimides with use temperatures as high as 800° F.

When the end cap compound reacts with the diamine, and the molar ratio of the ester, diamine, and end cap compound is n:n+1:2, the prepolymer formed is believed to have the structure:

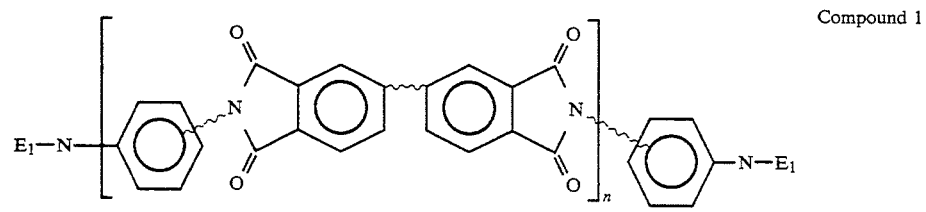

Compound 1

When the end cap compound reacts with the diamine, and the molar ratio of the ester, diamine, and end cap compound is n:n:1, the prepolymer formed is believed to have the structure:

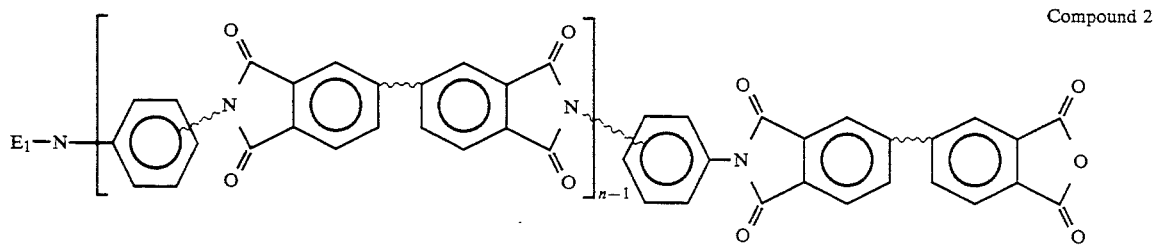

Compound 2

When the end cap compound reacts with the diamine, and the molar ratio of the ester, diamine, and end cap compound is n:n+1:1, the prepolymer formed is believed to have the structure:

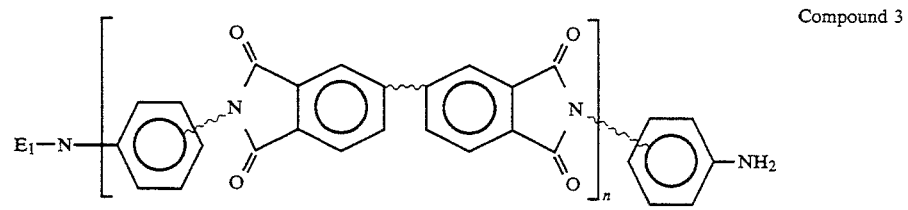

Compound 3

When the end cap compound reacts with the ester, and the molar ratio of the ester, diamine, and end cap compound is n+1:n:2, the prepolymer formed is believed to have the structure:

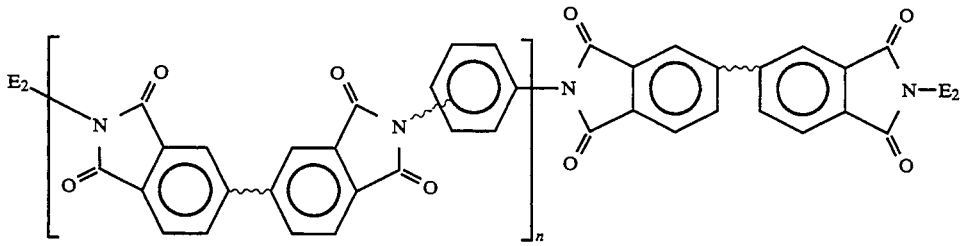

Compound 4

When the end cap compound reacts with the ester, and the molar ratios of the ester, diamine, and end cap compound are n+1:n:1, the prepolymer formed is believed to have the structure:

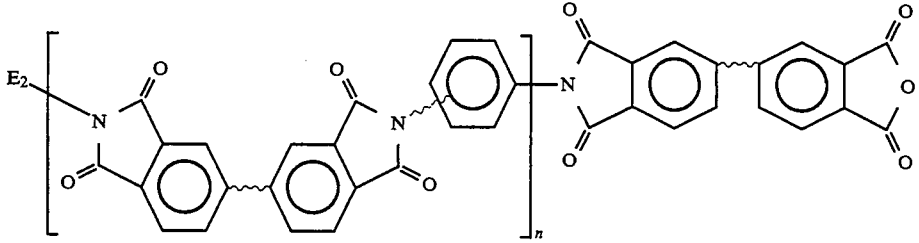

Compound 5

When the end cap compound reacts with the ester, and the molar ratios of the ester, diamine, and end cap compound are n:n:1, the prepolymer formed is believed to have the structure:

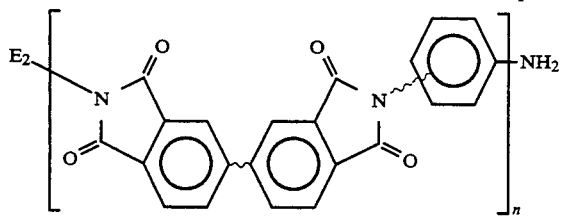

Compound 6

For compounds 1–6, the number "n" ranges between 2 and 20, and generally is sufficiently small that the molecular weight of the prepolymer is less than about 50,000, and preferably less than about 10,000.

For compounds 1–6, $E_1$ and $E_2$ are the end cap radicals provided by the end cap compound. The end cap radical has at least one unsaturated moiety and is capable of undergoing addition polymerization.

Macromolecular polyimides having a molecular weight greater than 50,000 are prepared when the imide prepolymers are heated at elevated temperature, generally at least about 600° F., and typically in the range of from about 600° to about 700° F. Heating takes place for a sufficient time to form crosslinked and thermally stable polyimide resins believed to have an average molecular weight in excess of 50,000. Because the product polyimide resin is cross-linked, the exact molecular weight of the resin is not known.

Preferably the polyimide resin is postcured by heating in air at a temperature of about 600° F. for about 16 hours, about 625° F. for about 2 hours, about 650° F. for about 4 hours, about 675° F. for about 2 hours, about 700° F. for about 4 hours, about 725° F. for about 2 hours, and about 750° F. for about 4 hours.

Applications

Polyimide resins of the present invention have many applications. For example, they can be reinforced with fiber to make light weight structural components such as aircraft engines and air frames. Among the fiber materials that can be used are carbon, including graphite; ceramics, including glass, quartz, alumina, silica, and silicon carbide; and refractory metals such as tungsten.

Another application for the polyimide resins is use as an adhesive, particularly as adhesives for joining high temperature composite structures made of polyimide resins.

The polyimide resins can also be used for molding, such as by injection molding or resin transfer molding. They can also be used as a protective coating for providing protection against high temperatures and/or oxidizing conditions.

Advantages

An important advantage of this present invention is that the polyimides described have significantly higher glass transition temperatures ($T_g$) than previously known polyimides. Above its glass transition temperature, a polymer loses much of its rigidity. Therefore, for a polymeric composite to be useful as a structural material, the resin's glass transition temperature must exceed the intended use temperature. Polyimides usually have glass transition temperatures of between 600° to 650° F. (as determined by measuring the inflection points of the dynamic storage modulus (G') curves, obtained by means of dynamic mechanical analysis). The glass transition temperatures of conventional addition polyimides can be increased moderately by heating the polyimides in air to temperatures at or exceeding 700° F. However, the $T_g$ cannot be raised much above 700° F. because substantial degradation occurs.

The glass transition temperature ($T_g$) of the new polyimides routinely exceed 800° F. and can surpass 840° F. All values for $T_g$ reported herein were obtained by measuring the inflection points of the dynamic storage modulus (G') curves obtained by means of dynamic mechanical analysis in accordance with ASTM D4065-82. The maximum temperature measurable by the dynamic mechanical analysis instrument was 842° F. The storage modulus curves of several specimens exhibited no sign of approaching an inflection point up to 842° F., indicating that the $T_g$ exceeded 842° F.

The extraordinarily high $T_g$ of these materials allows their use in load bearing structural applications with use temperatures exceeding 800° F. By contrast, the $T_g$ of currently available polyimides are substantially lower, with the $T_g$ of PMR-15 being at about 630° F., that of AF-R-700A at about 700° F., and that of AF-R-700B at about 750° F. Thus, none of current commercially available polyimide resins can be used at temperatures exceeding 800° F. Therefore, the present invention expands the application of polyimide composite technology to temperatures exceeding 800° F.

A second advantage of the present invention is the low raw materials cost of the initial reactants. In particular, the ester (a) and the phenylenediamine (b) are relatively inexpensive. In contrast, other high $T_g$ resins such as AF-R-700A and AF-R-700B, use expensive initial reactants, such as hexafluoroisopropylidene bis(phthalic anhydride).

A third advantage of the invention is the low toxicity of its initial reactants, the ester (a) and the phenylenediamine (b). The low toxicity minimizes health and safety risks in the preparation and processing of the materials. In contrast, the commonly used PMR-15 polyimide resin contains methylene dianiline, a known carcinogen.

A fourth advantage is the superior thermo-oxidative stability of composite panels fabricated from the new polyimides. Oxidative weight losses of panels subjected to 100 hours of exposure at temperatures of only about 700° F., ranged from about 0.67 to about 4.7 weight percent. In similar conditions, a composite panel fabricated from PMR-15 resin would lose over 10 percent by weight, while panels fabricated from AF-R-700A and AF-R-700B lose about 1.5 percent by weight.

A fifth advantage of the present invention is that the prepolymers (also known as intermediate polyimides) are readily processable using conventional autoclave equipment.

A sixth advantage of the present invention is that the prepolymers have commercially acceptable shelf life, in the order of at least 24 hours.

The combination of low material cost, low toxicity, and facile processability make the new polyimides unique and readily adaptable for many industrial applications.

That the new polyimides have such extraordinarily high glass transition temperatures and outstanding thermo-oxidative properties is very surprising to the inventors. It has been conventional wisdom that polyimides with high glass transition temperatures can be obtained only from para-substituted diamines.

It has been found that the combination of ester (a) and phenylenediamine (b) affords exceedingly high glass transition temperatures, despite the fact that meta-phenylenediamine is used. It is believed this results from the formation of an unusually strong interaction between ester (a) and the meta-phenylenediamine. It has also been observed that addition of para-phenylenediamine to meta-phenylenediamine prolongs the shelf life of the reaction mixture. Thus the use of a meta- and para-phenylenediamine mixture provides an optimal combination of processability and high temperature performance.

The following examples describe certain representative embodiments of the present invention.

EXAMPLE 1

Glass Fiber Prepreg and Molded Laminate

A mixture of 32.34 g (0.11 mole) biphenyldianhydride (BPDA) and 90 ml of anhydrous methanol was heated at reflux for 14.5 hours (the mixture became homogenous after about 11 hours), cooled to room temperature, and added to a mixture of 7.78 g (0.072 mole) of meta-phenylenediamine (MPDA) and 5.18 g (0.048 mole) para-phenylenediamine (PPDA) and 30 Ml of methanol. To this resulting mixture was added a solution of nadic monomethyl ester, prepared by reacting 1.64 g (0.01 mole) of nadic anhydride (NA) in 5 Ml of refluxing methanol for an hour and then cooled to room temperature. The resulting homogeneous solution contained 37% solids by weight and a ester:diamine:end cap ratio of 11:13:1.

The solution prepared above was used to impregnate 72 grams of S-2 glass fiber, using a drum winding machine. The resulting prepreg tapes were allowed to stand at room temperature for 16 hours, then dried at 150° F. for 1 hour. The dried prepreg tape was then sealed in a polyethylene bag and stored at 0° F. until further processing.

To effect curing, prepreg tapes were then placed in a mold and heated at 400° F. for one hour, whereupon, the monomers in the fiber reacted to form single end capped amine terminated, intermediate polyimides, and the volatile products of the reaction and residual methanol were evaporated. The prepreg was then placed (while hot) in a hydraulic press preheated to 500° F. The temperature of press was then gradually raised to 700° F. over a period of 45 minutes. When the mold temperature reached 475° F., a pressure of 200 psi was applied and maintained throughout the remainder of the molding cycle. The pressure dropped continuously to a temperature of about 530° F. due to melting and flow of the resin. When the mold temperature reached 700° F. it was held at this temperature for four hours, and then cooled to room temperature.

The resulting laminate was trimmed and then postcured without applied pressure, in air, at about 600° F. for about 16 hours, about 625° F. for about 2 hours, about 650° F. for about 4 hours, about 675° F. for about 2 hours, about 700° F. for about 4 hours, about 725° F. for about 2 hours, and about 750° F. for about 4 hours.

The resulting polyimide-glass composite panel exhibited virtually no voids as analyzed by microscopic analysis had a glass transition temperature of about 826° F., and a weight loss of about 2.35% by weight after 100 hours of exposure at 700° F. in air.

EXAMPLE 2

Alternative Molar Ratio

A solution containing ester:diamine:end cap in the molar ratio of 3.04:4.04:2 was formed, following the procedure of Example 1 above, using 24.99 g (0.085 moles) of BPDA, 6.1 g (0.056 moles) of MPDA, 6.1 g (0.056 moles) of PPDA, and 9.17 g (0.056 moles) of NA. The resultant solution was then used to impregnate 72 g of S-2 glass fiber as described in Example 1 above.

The prepreg thus formed was heated at 400° F. for one hour, whereupon, theoretically, double end cap intermediate polyimides were formed. The laminate was then cured following the procedure described in Example 1, with the exception of being held at 600° F. instead of at 700° F. for four hours prior to curing. The resulting laminate was postcured at about 600° F. for about 16 hours and at about 700° F. for about four hours.

The panel thus obtained exhibited no voids, a $T_g$ of about 753° F., and a weight loss of about 4.7% by weight after 100 hours of exposure at 700° F. in air.

EXAMPLE 3

A solution containing ester:diamine:end cap in a molar ratio of 9:10:1 was formed following the procedure of Example 1 above, using 39.69 g (0.013 moles) of BPDA, 16.2 g (0.15 moles) of MPDA, and 2.46 g (0.015 moles) of NA. The resultant solution was then used to impregnate 75 g of S-2 glass fiber as described in Example 1 above.

The prepreg thus formed was heated at about 400° F. for one hour, whereupon, theoretically, single end cap, amine terminated polyimides were formed. The laminate was then cured following the procedure described in Example 1. The resulting laminate was postcured under the same cycle as described in Example 1 with an additional postcure at about 775° F. for about two hours and at about 800° F. for about two hours.

The panel thus obtained exhibited virtually no voids, a $T_g$ in excess of 842° F., and a weight loss of about 4% by weight after 100 hours of exposure at 700° F. in air.

EXAMPLE 4

A solution containing ester:diamine:end cap in the molar ratio of 8:9:1 was formed, following the procedure of Example 1 above, using 35.28 g (0.12 moles) of BPDA, 11.66 g (0.108 moles) of MPDA, 2.92 g (0.027 moles) of PPDA, and 2.46 g (0.015 moles) of NA. The resultant solution was then used to impregnate 75 g of S-2 glass fiber as described in Example 1.

The prepreg thus formed was heated at 400° F. for one hour, whereupon, theoretically, single end cap, amine terminated polyimides were formed. The resulting laminate was then cured and postcured using the procedure described in Example 1. The panel thus obtained exhibited virtually no voids, a Tg in excess of about at least 842° F., and a weight loss of about 3.4% by weight after 100 hours of exposure at 700° F. in air.

EXAMPLE 5

A solution containing ester:diamine:endcap in the molar ratio of 13:14:1 was formed, following the procedure of Example 1 above, using 30.58 g (0.104 moles) of BPDA, 6.05 g (0.056 moles) of MPDA, 6.05 g (0.056 moles) of PPDA, and 1.31 g (0.008 moles) of NA. The resultant solution was then used to impregnate 72 g of S-2 glass fiber as described in Example 1.

The prepreg thus formed was heated at 400° F. for one hour, whereupon theoretically, single end cap, amine terminated polyimides were formed. The laminate was then cured following the procedure described in Example 1.

The panel thus obtained exhibited virtually no voids, a $T_g$ of about 665° F., and a weight loss of about 0.67% by weight after 100 hours of exposure at 700° F. in air.

Although the present invention has been described in considerable detail with regard to the preferred versions thereof, other versions are possible. Therefore, the appended claims should not be limited to the descriptions of the preferred versions contained herein.

What is claimed is:

1. A composition of matter comprising low molecular weight prepolymers suitable for chain extension and crosslinking to form high molecular weight, thermally stable polyimides, the prepolymers having the formula:

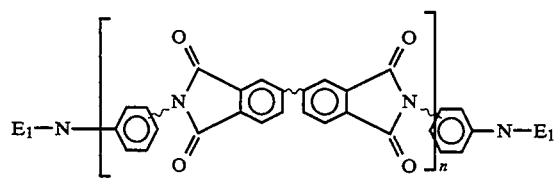

where (i) each $E_1$ is independently an end cap radical having at least one unsaturated moiety and being capable of undergoing addition polymerization, (ii) the nitrogen of the structure:

consists essentially of nitrogen in the meta- and para- positions, the ratio between the meta- and para- nitrogen being from about 3:2 to about 4:1, and (iii) n is at least 2 and is sufficiently small that the average molecular weight of the prepolymers is less than about 50,000.

2. A composition of matter comprising low molecular weight prepolymer suitable for chain extension and crosslinking to form high molecular weight, thermally stable polyimides, the prepolymers having the formula:

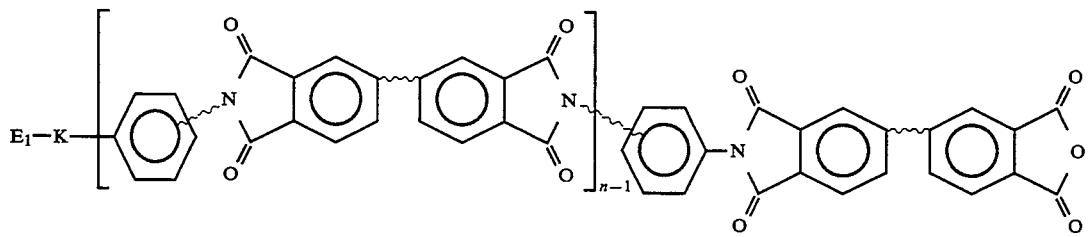

where $E_1$ is an end cap radical having at least one unsaturated moiety and being capable of undergoing addition polymerization, and n is at least 2 and is sufficiently small that the average molecular weight of the prepolymers is less than about 50,000.

3. A composition of matter comprising low molecular weight prepolymers suitable for chain extension and crosslinking to form high molecular weight, thermally stable polyimides, the prepolymers having the formula:

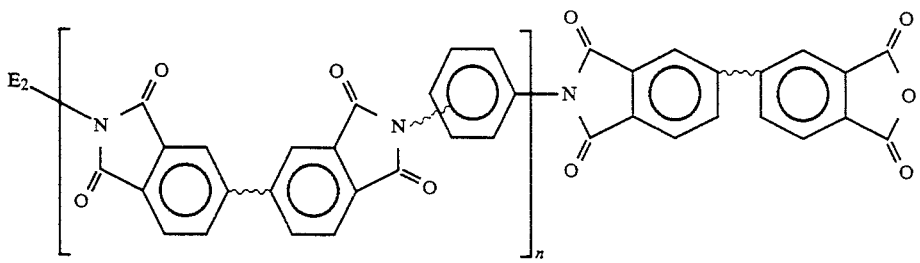

where $E_1$ is an end cap radical having at least one

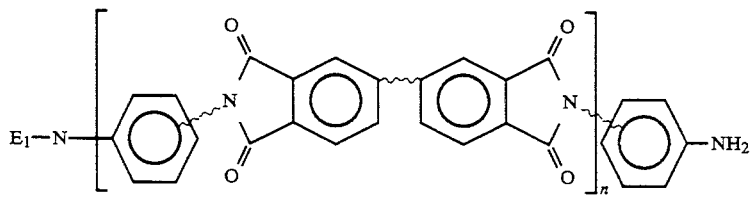

where $E_1$ is an end cap radical having at least one unsaturated moiety and being capable of undergoing addition polymerization, and n is at least 2 and is sufficiently small that the average molecular weight of the prepolymers is less than about 50,000.

4. A composition of matter comprising low molecular weight prepolymers suitable for chain extension and crosslinking to form high molecular weight, thermally stable polyimides, the prepolymers having the formula:

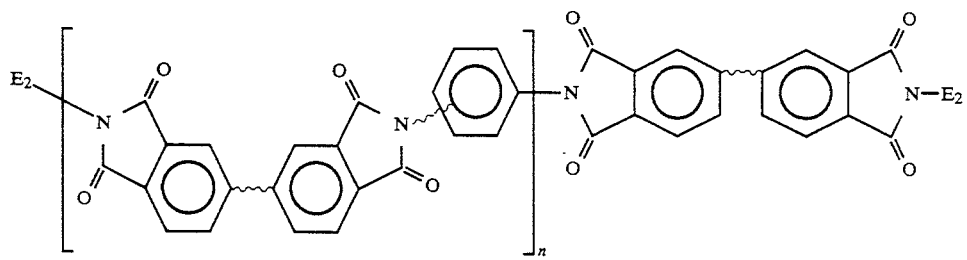

where (i) each $E_2$ is independently an end cap radical having at least one unsaturated moiety and being capable of undergoing addition polymerization,
(ii) the nitrogen of the structure:

consists essentially of nitrogen in the meta- and para- positions, the ratio between the meta- and para- nitrogen being from about 3:2 to about 4:1, and (iii) n is at least 2 and is sufficiently small that the average molecular weight of the prepolymers is less than about 50,000.

5. A composition of matter comprising low molecular weight prepolymers suitable for chain extension and crosslinking to form high molecular weight, thermally stable polyimides, the prepolymers having the formula:

where $E_2$ is an end cap radical having at least one unsaturated moiety and being capable of undergoing addition polymerization, and n is at least 2 and is sufficiently small that the average molecular weight of the prepolymers is less than about 50,000.

6. A composition of matter comprising low molecular weight prepolymers suitable for chain extension and crosslinking to form high molecular weight, thermally stable polyimides, the prepolymers having the formula:

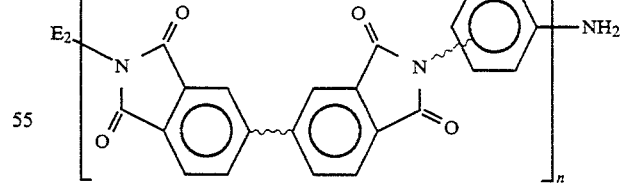

where $E_2$ is an end cap having at least one unsaturated moiety and being capable of undergoing addition polymerization, and n is at least 2 and is sufficiently small that the average molecular weight of the prepolymers is less than about 50,000.

7. A composition of matter consisting essentially of a mixture of the monomers:
(a) a dialkyl, trialkyl, or tetraalkylester of biphenyl-tetracarboxylic acid;

(b) phenylenediamine; and
(c) a divalent end cap compound characterized by (i) having at least one unsaturated moiety, (ii) being capable of reacting with the phenylenediamine or the ester to form an end cap radical that precludes further reaction of the phenylenediamine with the ester, and (iii) being capable of undergoing addition polymerization, wherein the ester (a), phenylenediamine (b), and end cap compound (c) are present in a molar ratio such that heating the mixture forms low molecular weight prepolymers having one end cap radical and suitable for chain extension and crosslinking to form high molecular weight, thermally stable polyimides, the prepolymers having the formula of either:

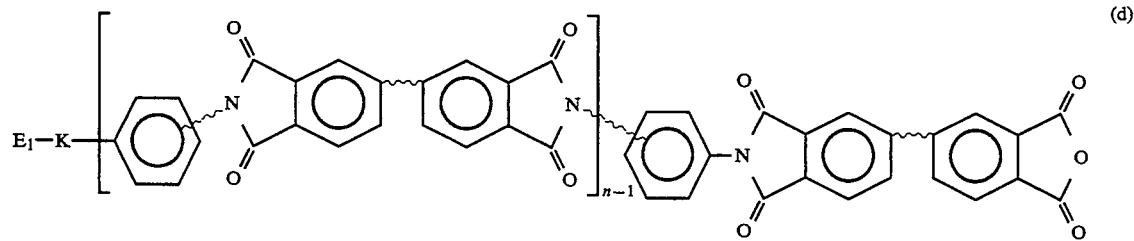
(d)

OR

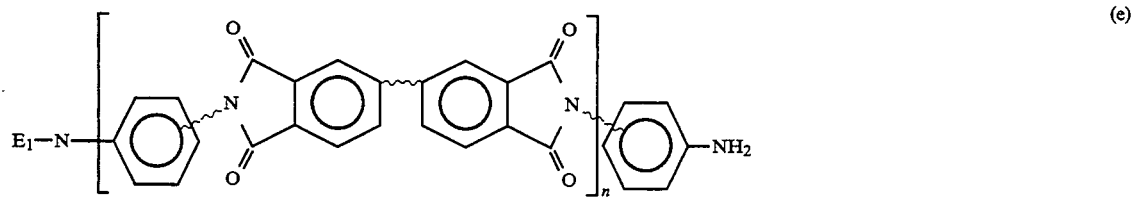
(e)

OR

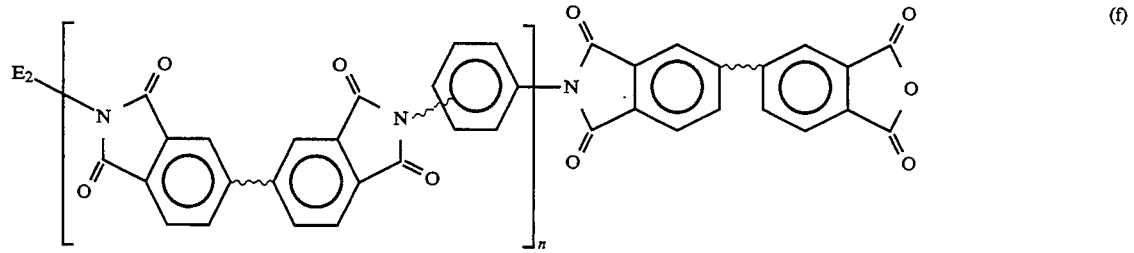
(f)

OR

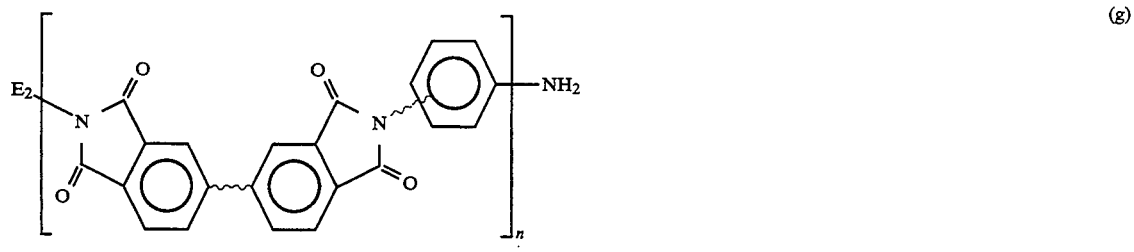
(g)

where $E_3$ is an end cap radical provided by the end cap compound when the prepolymers are of formula (d), $E_4$ is an end cap radical provided by the end cap compound when the prepolymers are of formula (e), $E_5$ is an end cap radical provided by the end cap compound when the prepolymers are of formula (f), and $E_6$ is an end cap radical provided by the end cap compound when the prepolymers are of formula (g), and n is at least 2 and is sufficiently small that the average molecular weight of the prepolymers is less than about 50,000.

8. A composition of matter consisting essentially of a mixture of the monomers:

(a) a dialkyl, trialkyl, or tetralkylester of biphenyltetracarboxylic acid;
(b) phenylenediamine, consisting essentially of meta-phenylenediamine mixed with para-phenylenediamine in the molar ratio of from about 3:2 to about 4:1; and
(c) a divalent end cap compound characterized by (i) having at least one unsaturated moiety, (ii) being capable of reacting with the phenylenediamine or the ester to form an end cap radical that precludes further reaction of the phenylenediamine with the ester, and (iii) being capable of undergoing addition polymerization, wherein the ester (a), phenylenediamine (b), and end cap compound (c) are present in a molar ratio such that heating the mixture forms low molecular weight prepolymers having two end cap radicals and suitable for chain extension and crosslinking to form high molecular weight, thermally stable polyimides, the prepolymers having the formula of either:

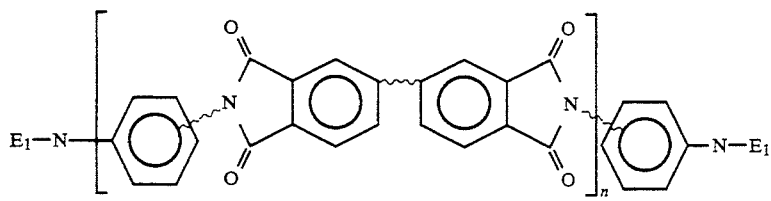

OR

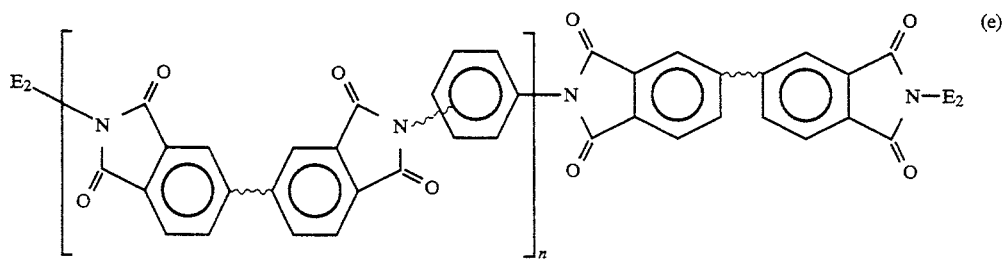

where $E_1$ is an end cap radical provided by the end cap compound when the prepolymers are of formula (d), $E_2$ is an end cap radical provided by the end cap compound when the prepolymers are of formula (e), and n is at least 2 and is sufficiently small that the average molecular weight of the prepolymers is less than about 50,000.

9. A composition of matter consisting essentially of a mixture of compounds:

(a) an ester of the formula:

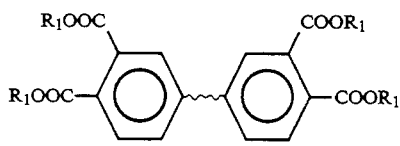

wherein each $R_1$ is independently selected from a group consisting of alkyl and hydrogen; at least two $R_1$ are alkyl;

(b) phenylenediamine; and
(c) a divalent end cap compound selected from the group consisting of (i) a mono or dialkyl ester of a dicarboxylic acid, and (ii) an aromatic amine; and wherein the molar ratio of a:b:c is such that heating the mixture forms a low molecular weight prepolymer having one end cap radical and suitable for chain extension and crosslinking to form high molecular weight, thermally stable polyimides.

10. A composition of matter consisting essentially of a mixture of compounds:

(a) an ester of the formula:

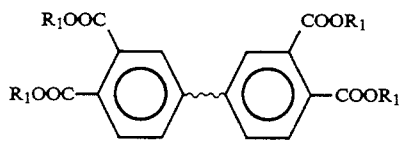

wherein each $R_1$ is independently selected from a group consisting of alkyl and hydrogen; at least two $R_1$ are alkyl;

(b) phenylenediamine, consisting essentially of meta-phenylenediamine mixed with para-phenylenediamine in the molar ratio of from about 3:2 to about 4:1; and (c) a divalent end cap compound selected from the group consisting of (i) a mono or dialkyl ester of a dicarboxylic acid, and (ii) an aromatic amine; and wherein the molar ratio of a:b:c is such that heating the mixture forms a low molecular weight prepolymer having two end cap radicals and suitable for chain extension and crosslinking to form high molecular weight, thermally stable polyimides.

11. The composition of matter of claim 9, wherein the end cap (c) is a mono or dialkyl ester of a dicarboxylic acid, and wherein the molar ratio of a:b:c: is n:n:1, and wherein n is of from 2 to about 20.

12. The composition of matter of claim 9, wherein the end cap (c) is a mono or dialkyl ester of a dicarboxylic acid, wherein the molar ratio of a:b:c: is n:n+1:1, and wherein n is of from 2 to about 20.

13. The composition of matter of claim 9, wherein the end cap (c) is an aromatic amine, wherein the molar ratio of a:b:c: is n+1:n:1, and wherein n is of from 2 to about 20.

14. The composition of matter of claim 9, wherein the end cap (c) is an aromatic amine, wherein the molar ratio of a:b:c: is n:n:1, and wherein n is of from 2 to about 20.

15. The composition of matter of any one of claims 7, 9, 11, 12, 13 or 14 wherein the phenylenediamine consists essentially of meta-phenylenediamine alone, or sufficient meta-phenylenediamine mixed with para-phenylenediamine, so that the composition has a shelf life of at least 24 hours.

16. The composition of matter of claim 15 wherein the molar ratio of meta-phenylenediamine: para-phenylenediamine is from about 1:0 to about 1:1.

17. The composition of matter of claim 15 wherein the molar ratio of meta-phenylenediamine: para-phenylenediamine is from about 3:2 to about 4:1.

18. The composition of matter of claim 9 or 10 wherein the molar ratio of meta-phenylenediamine: para-phenylenediamine is about 1:1.

19. A polyimide resin having a molecular weight greater than 50,000 prepared by the steps of heating the composition of matter of any one of claims 7–14 to form prepolymers and crosslinking the formed prepolymers.

20. A polyimide resin having a molecular weight greater than 50,000 prepared by the steps of heating the composition of matter of claim 15 to form prepolymers and crosslinking the formed prepolymers.

21. An article of manufacture comprising fibers impregnating a polyimide resin matrix having a molecular weight greater than 50,000 and prepared by the steps of heating the composition of matter of any one of claims 7–14 to form prepolymers and crosslinking the formed prepolymers.

22. An article of manufacture comprising fibers impregnating a polyimide resin matrix having a molecular weight greater than 50,000 and prepared by the steps of heating the composition of matter of claim 15 to form prepolymers and crosslinking the formed prepolymers.

23. The polyimide resin of claim 19 having a $T_g$ greater than 800° F.

24. The polyimide resin of claim 23 having a weight loss of less than 5 percent when heated in air at 700° F. for 100 hours.

25. The polyimide resin of claim 20 having a $T_g$ greater than 800° F.

26. The polyimide resin of claim 25 having a weight loss of less than 5 percent when heated in air at 700° F. for 100 hours.

27. The composition of claim 2, 3, 5, or 6 wherein the nitrogen of the structure:

 (1)

consists essentially of nitrogen in the meta- and para-positions, the ratio between the meta- and para-nitrogen being from about 3:2 to about 4:1.

28. The composition of claim 27 wherein sufficient nitrogen in the structure (1) is in the meta-position that the composition has a shelf life of at least 24 hours.

29. The composition of claim 1 or 4 wherein sufficient nitrogen in the structure:

is in the meta-position that the composition has a shelf life of at least 24 hours.

30. The composition of claim 8 or 10 comprising sufficient meta-phenylenediamine that the composition has a shelf life of at least 24 hours.

* * * * *